United States Patent [19]

Gottlieb

[11] Patent Number: 4,876,193
[45] Date of Patent: Oct. 24, 1989

[54] DETERMINATION OF SUPPRESSOR FUNCTIONAL RESERVE

[75] Inventor: A. Arthur Gottlieb, New Orleans, La.

[73] Assignee: Imreg, Inc. (Delaware corporation), New Orleans, La.

[21] Appl. No.: 832,016

[22] Filed: Feb. 24, 1986

[51] Int. Cl.$^4$ ............................ C12Q 1/02; C12N 5/00
[52] U.S. Cl. .................................... 435/29; 435/240.2; 435/948
[58] Field of Search ................. 435/29, 2, 34; 424/88, 424/101

[56] References Cited

U.S. PATENT DOCUMENTS 4,728,614 3/1988 Lau .......................................... 435/68
4,778,750 10/1988 Gottlieb ................................. 435/29

Primary Examiner—Robert J. Warden
Assistant Examiner—Janelle Graeter
Attorney, Agent, or Firm—Richard H. Stern

[57] ABSTRACT

Methods are described for assaying, in vitro, the capacity of a subject's lymphocytes to manifest suppressor function. PBLs are exposed to an agent stimulating suppressor cell formation and/or activation. Other PBLs are treated to induce a cell proliferative response, thereby producing responder cells. The responder cells are subjected to an antigen in the presence of the suppressor cells previously produced and in the presence of various concentrations of an amplifier. The procedure provides a means of ascertaining suppressor capacity of the subject's immune system, i.e., the subject's potential to express suppressor function, thereby permitting assay of severity of autoimmune disease, titrating dosage of immunomodulatory agents, and determining whether modulator therapy is feasible.

20 Claims, No Drawings

DETERMINATION OF SUPPRESSOR FUNCTIONAL RESERVE

BACKGROUND

One important aspect of the human and animal immune system is the negative regulation of the immune responses that occur in response to the apparent presence of antigens. If no brake were placed on immune response, antibody-producing cells, for one example, would continue producing antibodies indefinitely. When the immune system is not appropriately regulated, several systemic malfunctions can occur. Defects of the operation of the immune system such as these have been associated with certain autoimmune disorders, in which the body reacts against its own tissue as if the tissue were a foreign body. Rheumatoid arthritis, multiple sclerosis, myasthenia gravis, lupus erythematosus, and insulin-dependent diabetes (type 1) are believed to be examples of such conditions.

The negative regulation of the immune system is believed to be controlled in part by cells known as "suppressor cells." Human suppressor cells include T8 cells (also known as T8+ cells); there may be other human suppressor cells. Suppressor cells act in concert with other cells to bring about a normal immune response, what may be considered immune system homeostasis. Autoimmune defects of the type described above may result from insufficient production, potentiation, or operation (which are collectively referred to at times hereinafter as "activation") of suppressor cells. It is therefore useful to assay suppressor cell function, and in particular to assay the maximum capacity of a suppressor cell population to be activated. However, convenient, inexpensive, in vitro diagnostic tests for diagnosing or assaying suppressor cell function are presently unavailable. In particular, quantitative tests are presently unavailable.

A copending patent application of the inventor (Gottlieb, "Diagnostic Methods for Immune Function," U.S. patent application Ser. No. 830,728, now issued as U.S. Pat. No. 4,778,750) describes a method for assaying amplifier immune reserve, a function of the human and animal immune system in some respects similar to that of the present invention. An abstract published in March 1985 (Sizemore, Farmer, and Gottlieb, "Enhancement of nonspecific suppressor T cell activity by immunomodulators derived from human leukocyte dialysates," Fed. Proceedings 947, No. 3133) refers in general terms to various aspects of the procedures described herein. Other background on amplifiers and suppressors is found in Gottlieb U.S. Pat. No. 4,468,379, in copending Gottlieb U.S. patent application Ser. No. 643,724 now issued as U.S. Pat. No. 4,616,099, and in copending Gottlieb U.S. patent application Ser. No. 813,632, now issued as U.S. Pat. No. 4,699,898.

A known method of cultivating suppressor cells is to expose normal lymphocytes to a plant product known as concanavalin A (Con A), which in certain concentrations induces the production of suppressor cells. By culturing lymphocytes with Con A, suppressor cells can be produced. See generally Shou, Schwartz, and Good, *Suppressor cell activity after concanavalin A treatment of lymphocytes from normal donors,* 143 J. Exp. Med. 1100 (1976); Birnbaum and Swick, *Human suppressor lymphocytes,* 40 Cell Immunol. 16 (1978). It is also known that proliferation of cells may be inhibited by administration of such agents as mitomycin, which interferes with cell division.

SUMMARY OF THE PRESENT INVENTION

The present invention is an in vitro test method for determining the magnitude of an immune response function of an animal or human subject by assaying the capacity of the subject's lymphocytes to manifest suppressor function. In particular, the invention permits the measurement of "suppressor immune reserve" (i.e., remaining suppressor capacity) in a subject with an impaired immune system, such as that associated with an autoimmune disorder or a hypernormal immune response to actual foreign antigen or to body cells incorrectly perceived as antigens.

The procedure of this invention begins with isolation, by known procedures, of peripheral blood lymphocytes (PBLs, also referred to as peripheral blood mononuclear cells), taken from the test subject. These PBLs are exposed in vitro to Con A or another mitogen or agent that stimulates suppressor cell formation and/or activation, and concurrently to several dilutions of amplifier and also a saline control (i.e., 0% amplifier). The various samples are cultivated, and varying amounts of suppressor cells are activated, depending on the concentration of amplifier and the condition of the test subject's immune system.

The remaining Con A, if any, is then removed from the cultures with alpha methylmannoside. Then the cultures are treated with mitomycin or another agent (such as radiation) that prevents the suppressor cells in the cultures from dividing further. The residual mitomycin, if any, is then eliminated, leaving a preparation containing suppressor cells that will not engage in further proliferation (cell division).

The preparation is mixed with a fresh PBL population (designated hereinafter at times as "responder cells") obtained either from the test subject or from a healthy donor. This PBL population is not treated with Con A or mitomycin, and it is capable of cell division. The mixture is exposed to another mitogen, such as phytohemoagglutin (PHA), pokeweed (PWM), or an antigen, such as tetanus toxoid, to induce a cell proliferative immune response in the PBLs of the mixture that have not been treated with mitomycin.

Although the untreated responder PBLs will proliferate in response to the second mitogen, the magnitude of that response will be partially suppressed and thus decreased by the Con-A-activated suppressor cells from the test subject PBLs. Moreover, the reduction in proliferative response will be proportional to the amount of suppressor activity induced in the test subject's PBLs. On the other hand, the amount of suppressor activity can be enhanced by inclusion of a leukocyte-derived immunomodulator, as for example those described in the '724 patent application.

The extent of the suppression is measured by assaying the proliferative response of the responder cells to mitogen or antigen, by measuring proliferative response directly or by measuring the production of a material associated with immune response such as interleukin-2 (IL-2), since the lens of the material produced, the more suppression, and vice versa. The production of IL-2 in response to mitogen is a convenient index of immune response, and its production may be assayed by measuring thymidine uptake, where the thymidine is radioactively or fluorescently tagged to facilitate its measurement, into an IL-2 response cell line such as CTLL-2, as described in the inventor's co-pending application "Diagnostic Methods for Immune Function." Another index is production of gamma-interferon, as is generation of cytotoxic lymphocytes. Production of gamma-interferon or IL-2 can also be assayed by an ELISA assay. The use of IL-2, thymidine, gamma-interferon, and ELISA assays are all discussed in the previously cited copending Gottlieb patent application for "Diagnostic Methods for Immune Function," among other places.

Accordingly, the foregoing procedure furnishes a method of assaying suppressor capacity of a subject's immune system, which is to say the maximum remaining potential of a test subject's PBLs to express suppressor activity. That information may be used for a variety of medical purposes, including determining the severity of a particular autoimmune disorder, titrating the administration of chemotherapeutic and/or immunomodulatory agents, and determining whether certain therapeutic measures are feasible.

DETAILED DESCRIPTION OF PREFERRED EMBODIMENT

The procedure of this invention provides a means of assaying immune function, specifically suppressor immune reserve. The basic steps are removal of blood from the animal or human subject, preparation of purified peripheral blood mononuclear cell (PBL) populations, addition of the mitogen ConA to the purified PBL populations (with and without amplifier reagent), cultivation of PBLs, treatment with mitomycin, addition of further PBLs, and assay of a suitable measure of immune function such as mitogen-induced cell proliferation, IL-2 production, or gamma-interferon production.

I.

Isolation and fractionation of peripheral lymphocytes

Venous blood was extracted from test subjects. An appropriate sample is approximately 20 to 25 ml/patient. Data presented below is based on samples from four normal human test subjects.

EXAMPLE 1

Isolation of PBLs

Peripheral blood mononuclear cells (PBLs) were obtained from heparinized blood samples of a test subject, by density gradient centrifugation on Lymphocyte Separation Medium (LSM) (Litton Bionetics, Kensington, MD). The cells of interest are those found at the interface.

The PBLs are washed 2× in 0.15M saline and 1× in RPMI-1640 medium containing 25 mM HEPES (GIBCO, Grand Island, NY), and are then resuspended to $1 \times 10^6$ cells/ml in the latter, supplemented with 10%- normal human AB+ serum, 2 mM L-glutamine (GIBCO), and 2% penicillin-streptomycin-neomycin antibiotic mixture (PSN antibiotic mixture, GIBCO). The resulting cell preparation is set aside.

II.

ACTIVATION AND CULTURE OF SUPPRESSOR CELLS

A. Activation with Con A

The preparation of Example 1 is then activated with Con A or another agent that activates suppressor cells. The preparation is divided into parts and concurrently exposed to various dilutions of amplifier. Suitable amplifiers include Amplifier Beta of the '099 patent, Amplifier Zeta-2 of the '099 patent, and TGG of the '898 patent.

EXAMPLE 2

Con A activation of cells

Con A (Concanavalin A, Sigma Chem. Co., St. Louis, No. C-2010, Type IV) is prepared as a 1 mg/ml stock in saline, and the concentration is verified spectrophotometrically (E=1.14 at 280 nm, 1 cm path length).

A sample of the cell preparation of Example 1 is mixed with a volume of a dilution of Con A stock that reduces Con A concentration to 0.2 to 0.5 ug/ml in the final preparation. The Con A-treated cells are set aside for the procedure of the next Example.

B.

ADDITION OF BETA, CULTIVATION

Preparations of Amplifier Beta of the '099 patent, Example 7 (the product concentration being that amount of amplifier derived from $400 \times 10^6$ buffy coat leukocytes, in each 1 ml of aqueous saline) were diluted with aqueous saline to provide the following reagents:

| Reagent | A | B | C | D | E | F |
|---|---|---|---|---|---|---|
| Dilution, 1: | 500 | 1000 | 2000 | $10^4$ | $10^5$ | $10^6$ |

Reagent G was prepared, also, consisting of sterile normal saline.

The dilutions of Reagents A, B, C, D, E, and F correspond approximately to the amount of Amplifier Beta recovered by the process of the '099 patent from 800,000, 400,000, 200,000, 40,000, 4000. and 400 leukocytes, respectively. The inventor has determined empirically that those dilutions described below in examples, are satisfactory to accomplish the kind of assay described hereinafter. (Reagents A, B, and C were used for one test subject and Reagents D, E, and F were used for a second.) Those skilled in the art will appreciate, however, by examining the data tabulated below, that other, as well as more or fewer, dilutions of this type may be selected to accomplish the kind of results one desires, using this disclosure as a guide. (For example, more closely spaced dilutions—such as 1:200, 300, 400, 500, 600, 800, 1000, 1200, 1500, 1800, 2000, 2400, 3000—may more precisely measure the maximum immune function parameter (such as IL-2 production) achievable. That procedure, however, will also (1) require extraction of more blood from the test subject and (2) be more laborious and costly.) Accordingly, the inventor does not consider the invention to be limited to the particular quantities of reagent specified in the examples. Rather, the invention includes the use of such other proportions, as well, that the disclosure would teach a skilled person to utilize with necessary experimentation as suggested by the disclosure.

EXAMPLE 2A

Adding Amplifier Beta and culturing cells (Subject #1)

To 20 ml of the Con-A treated cell preparations of Example 2A is added 20 ul of Reagent A. Four 5-ml samples of the resulting material are placed in 60 mm culture dishes (Corning, Corning, NY). [The letter u is used hereinafter to mean "micro" as in ul (microliters) and ug (micrograms).]

The same procedure is repeated successively with Reagents B, C, and G (control).

The dishes of cells are incubated for 48 hr at 37° C. in a 5% $CO_2$ in air atmosphere. Cells are harvested and washed 3× with 0.2M alpha methyl mannoside (Sigma Chem. Co., Grade II, M-3752, St. Louis) in HBBS (Hanks Balanced Salt Solution, GIBCO) to remove residual Con A. (A, B, C, and G reagents are kept separate from one another.)

EXAMPLE 3

Exposure to and removal of mitomycin

Cells are resuspended to approximately $10^7$ cells/ml in HBSS and are treated with mitomycin C (Sigma Chem., M-0503) at a final concentration of 50 ug/ml for 45–60 min at 37° C., in an atmosphere of 5% $CO_2$. This followed with 3× washes with cold HBSS with 2% AB+ serum.

The cells are resuspended in RPMI-1640 medium containing 25 mM HEPES supplemented with 10% AB+ serum and 2% PSN, and they are incubated for 1 hr at 37° C. to allow for the release of any residual mitomycin C in culture. The cells are then washed 2× in RPMI-1640 and resuspended to $1.5 \times 10^6$ cells per ml in RPMI-1640 medium containing 25 mM HEPES supplemented with 10% AB+ serum and 2% PSN. The suspension is set aside. (As before, A, B, C, and G reagents are kept separate from one another.)

III.

BIOASSAY

The non-proliferating suppressor culture of Example 3 is then mixed with a fresh PBL. Preferably, the test subject's PBLs should be used to avoid introducing another possible variable. But this is not always feasible, and therefore a PBL from a normal donor may be used. The new PBL is mixed with the culture of Example 3, exposed to a material (such as PHA) that will cause a cell proliferative response, and the proliferative response, as an index of immune function, is assayed.

EXAMPLE 4

Preparation of cultures for assay of suppressor reserve

Fresh PBLs of Example 1 are resuspended to $1.5 \times 10^6$ cells/ml in RPMI-1640 medium containing 25 mM HEPES supplemented with 10% AB+ serum and 2% PSN, thereby providing a Responder Preparation. The responder cells are dispensed in 0.1 ml volumes into wells of a 96-well microtiter plate (Falcon #3072, Becton Dickinson, Oxnard, CA).

The suspensions of Example 3 are dispensed in 0.1 ml volumes into the wells containing the responder cells. It is desirable to do the procedure in triplicate or quadruplicate in order to average out error, so that 12–16 wells will be used.

A suitable concentration of mitogen, such as PHA (Wellcome Reagents HA16) or Pokeweed Mitogen (GIBCO, Grand Island, NY) or Con A is added to each well, in a volume of approximately 20 ul/well. A suitable concentration in the well of PHA for this purpose is 0.25 ug/ml. A suitable concentration in the well of Con A for this purpose is 1.0 ug/ml.

The plates are then incubated for 72 hr at 37° C. in a 5% $CO_2$ in air atmosphere. At 18 hours before conclusion, 20 ul/well of 20 uC/ml tritiated thymidine (New England Nuclear, Boston MA) is added to each well.

The wells are subsequently harvested onto glass fibre filter strips (M.A. Bioproducts, Walkersville MD) and the resultant counts per minute (cpm) are determined by liquid scintillation counting.

Uptake of radioactive thymidine was used as a convenient measure of cell proliferation ("cell proliferation index") because it is relatively inexpensive and readily available. Uptake of other DNA precursors, such as deoxycytidine, could be used as a cell proliferation index, but they are believed to be not as convenient. Also, as indicated in the copending application "Diagnostic Methods for Immune Function," production of IL-2 is associated with cell proliferation. Hence, the amount of IL-2 generated by a cell preparation may be measured (for example, by measuring the thymidine uptake of such cells as CTLL-2 when the latter are exposed to a supernatant taken from the culture to be assayed for cell proliferation) to provide a cell proliferation index.

The following quantities are defined for the purposes of the assay of Example 4:

Corrected cpm = Mean cpm with mitogen − mean cpm without nitrogen

% suppression = 100[1 − (corrected cpm with Con A-activated cells exposed to amplifier)/(corrected cpm with Con A-activated cells not exposed to amplifier)]

The % suppression results for Test Subject No. 1, for various dilutions of Amplifier Beta are as shown below:

TABLE 1

Modulation of Suppressor Activity by Various Dilutions of Amplifier Beta (Subject #1)

| Reagent | A | B | C | G |
|---|---|---|---|---|
| Dilution, 1: | 500 | 1000 | 2000 | (control) |
| % Suppression | 66% | 42% | 77% | 0% |

The foregoing procedure was carried out with a second test subject, using Reagents D, E, and F, as well as Reagent G (control).

EXAMPLE 5

Assay with Beta (Subject #2)

The procedure of Examples 1 to 4 was repeated with a second test subject, but in Example 2A Reagents D, E, and F were used in place of Reagents A, B, and C. The results of the assay are shown in Table 2.

TABLE 2

Modulation of Suppressor Activity by Various Dilutions of Amplifier Beta (Subject #2)

| Reagent | D | E | F | G |
|---|---|---|---|---|
| Dilution, 1: | $10^4$ | $10^5$ | $10^6$ | (control) |
| % Suppression | 57% | 11% | 0% | 0% |

IV.

USE OF OTHER ASSAY AMPLIFIERS

The procedure of this invention may be carried out with other amplifiers, as well as with Amplifier Beta. Dilutions of Amplifier Zeta-2 of the '099 patent were prepared from amplifier derived from $400 \times 10^6$ leukocytes per ml aqueous saline. That preparation was further diluted with aqueous saline to provide the following additional reagents:

| Reagent Dilution, 1: | H 1000 | I 5000 | J $10^4$ | K $10^5$ | L $10^6$ |
|---|---|---|---|---|---|

As before, Reagent G was sterile saline.

EXAMPLE 6

Assay with Zeta-2 (Subject #3)

The procedure of Examples 1 to 4 was repeated with a second test subject, but in Example 2A Reagents H, I, and J were used in place of Reagents A, B, and C. The results of the assay are shown in

EXAMPLE 7

Assay with Zeta-2 (Subject #4)

The procedure of Examples 1 to 4 was repeated with a second test subject, but in Example 2A Reagents J, K, and L were used in place of Reagents A, B, and C, and 1.0 ug/ml Con A was used to induce cell proliferation in the responder culture. In the other examples herein (Examples 4, 5, and 6), the responder cultures were stimulated with 0.25 ug/ml PHA. The results of the assay are shown in Table 3.

TABLE 3

Modulation of Suppressor Activity
by Various Dilutions of Amplifier Zeta-2

| Subject #3 | | | | |
|---|---|---|---|---|
| Reagent | H | I | J | G |
| Dilution, 1: | 1000 | 5000 | $10^4$ | (control) |
| % Suppression | 0% | 12.8% | 29.5% | 0% |
| Subject #4 | | | | |
| Reagent | J | K | L | G |
| Dilution, 1: | $10^4$ | $10^5$ | $10^6$ | (control) |
| % Suppression | 38.3% | 47.1 | 13% | 22.2% |

Preparations of TGG are prepared, to repeat the procedure described above. TGG, purified in accordance with the procedures of the cited co-pending '898 patent, is prepared to various dilutions. The starting dilution is 1:500, which is approximately $3 \times 10^{-10}$M. Reagents M, N, and O are prepared, with further TGG dilutions of 1 to 1000, 2000, and 4000, respectively. As before the control is Reagent G.

EXAMPLE 8

Assay with TGG

The procedure of Examples 1 to 4 is repeated, but in the procedure of Example 2A Reagents M, N, and O are used in place of Reagents A, B, and C. The results of the assay are comparable to those of Examples 1 to 4.

As previously indicated, with reference to assay of cell proliferative response, an alternative assay method may be used in which thymidine is tagged with another measuring means, such as a fluorescent dye or fluorescent antibody. Moreover, ELISA assays may be used instead. As indicated above, an IL-2 assay is also a suitable index; use of a gamma-interferon assay is also appropriate.

V.

THERAPEUTIC UTILIZATION OF TEST

It is clear from the preceding tables that amplifiers have the ability to modify the suppressor response of lymphocytes. The inventor theorizes that amplifiers operate to suppress immune response through activation of a subpopulation of T4 cells known as suppressor-inducer cells. The inventor further theorizes that the immune response to mitogen caused by administration of amplifier is a mixture of positive ("amplifier") and negative ("suppressor") effects, with the latter preponderating in a dosage zone that may be referred to as the "paradoxical response" range. The inventor has observed, and the previously cited pending patent applications note, that, when a range of concentrations of amplifier is applied to a test subject's PBLs, the magnitude of immune response decreases after a certain concentration is reached. That is, the immune response increases with increasing concentration of amplifier through a range that may be designated the "nonparadoxical response" concentration range, but after a maximum response is reached, further increasing concentrations of amplifier merely decrease the immune response; this is the "paradoxical response" concentration range.

In any event, the observed decrement in proliferative response to mitogen is believed to be a reflection of the potential ability of the patient's suppresor cells to be activated, and therefore a range of concentrations provides a measure of the maximum potential capacity of such cells to be activated. That is to say, the decrement in proliferative response is a measure of the reserve (but previously unutilized) capacity of the PBLs to produce suppressor cells and/or manifest suppressor function, and by inference to produce other immunoregulatory materials having a suppressive effect on the immune system.

As indicated earlier, the invention disclosed herein provides an in vitro means of assaying human and animal immune response in a number of circumstances where such assays are useful for medical and veterinary purposes. (As indicated in the '099 patent, methods applicable to human subjects may be adapted to animal subjects to accomplish the same purposes.) The following examples are intended to illustrate the use of the assay method described above. In these examples, the following terminology is at times used: "suppressor immune reserve" refers to the maximal suppressor response caused by the procedures described above. "Base suppressor response" refers to the suppressor response caused by mitogen Con A alone (such as by use of Reagent G in the Examples).

EXAMPLE 9

Determination of suppressor immune reserve

PBLs from a patient with immune system dysfunction associated with rheumatoid arthritis are assayed in accordance with Examples 1 to 4. The attending physician determines that the patient's suppressor immune reserve is sufficient to make it advisable, in the physician's medical judgment, to attempt to restore it by administration of an amplifier. (For example, suppressor immune reserve above 40%.)

EXAMPLE 10

Suppressor immune reserve of second patient

PBLs from a second patient with immune system dysfunction associated with rheumatoid arthritis are assayed in accordance with the same procedure. The attending physician determines that the patient's suppressor immune reserve is insufficient to make it advisable, in the physician's medical judgment, to attempt to restore it by administration of an amplifier. (For example, suppressor immune reserve below 10%.) No amplifier treatment is attempted.

EXAMPLE 11

Titration of amplifier dosage

The physician of Example 9 administers to the patient of Example 9 a daily dosage of Amplifier Beta of Example 7 of the '724 application equivalent to that derived from 40 million leukocytes. After one week the physician reassays the patient's immune response in accordance with the foregoing procedure. The physician determines, in his or her medical judgment, that the base immune response has now been restored to an acceptable level. (For example, base suppressor response of at least 50% of tested suppressor immune reserve.)

Thereafter, the physician administers to the patient a weekly dosage of Amplifier Beta equivalent to that derived from 40 million leukocytes.

At monthly intervals, the physician reassays the patient's base suppressor response and makes a determination whether the dose of Amplifier Beta should be increased or decreased, in order to maintain the base suppressor response at an acceptable level.

EXAMPLE 12

Extreme reaction to poison ivy

A patient displays a hypernormal reaction to poison ivy or another hypernormal cell-mediated immune reaction to foreign antigen. The attending physician suspects a systemic dysfunction of the patient's suppressor function.

The physician performs an assay in accordance with the procedure of Example 9 and confirms the suspicion. The patient's suppressor immune reserve is not abnormally low, but the patient's base suppressor response is significantly below normal. (For example, suppressor immune reserve is at least approximately 40%; base suppressor response is less than 20%.)

The physician administers Amplifier Beta or Amplifier Zeta-2 in the paradoxical response concentration range. For example, the physician administers to the patient every two days a dosage of Amplifier Beta of Example 7 of the '724 application equivalent to that derived from 40 million leukocytes. Treatment continues until base suppressor response is restored to at least approximately 45%.

The foregoing assay procedure may be expanded to use in cows, pigs, and other animals, by extrapolation from the data on human beings, in a manner that will be obvious to those skilled in the art.

GENERAL CONCLUDING REMARKS

The above described procedures disclose what the inventors believe is a unique and hitherto unknown method of assaying human or animal immune system suppressor response. While the invention has been described primarily in connection with a specific and preferred embodiment thereof, it will be understood that it is capable of further modifications without departing from the spirit and scope of the invention. This application is intended to cover all variations, uses, or adaptations of the invention, following, in general, the principles of the invention and including such departures from the present disclosure as come within known or customary practice within the art to which the invention pertains, or as are obvious to persons skilled in the art, at the time the departure is made.

As used in the claims, the term "cell proliferation index" means a measure of cell proliferation. Such a measure can be a direct measurement of cell proliferation, as for example, by measuring cell uptake of a material associated with cell proliferation, such as by measuring thymidine uptake. Those skilled in the art will recognize that other DNA precursors may be utilized in lieu of thymidine, such as deoxycytidine, deoxyadenosine, or other DNA precursors. (Those skilled in this art will recognize that such DNA precursors are equivalents of thymidine in the claims.)

As used in the claims, the term "autoimmune condition" includes the "collagen diseases," which thos skilled in the art understand to have significant autoimmune components.

The term "maximum % suppression" means the maximum (i.e., highest) value observed for % suppression, as "% suppression" is defined and discussed on p. 12 of the specification, supra.

The term "% suppression assay results" means the results of assays measuring "% suppression," as "% suppression" is defined and discussed on p. 12 of the specification, supra.

The term "maximum % suppression assay results" means the maxiumum (i.e., highest) value of the results of assays measuring "% suppression," as "% suppression" is defined and discussed on p. 12 of the specification, supra.

The term "paradoxical response concentration range" refers to the discussion on pp. 15-16 of the specification, concerning the fact that when a range of concentrations of amplifier is applied to a test subject's PBLs, the magnitude of immune response decreases after a certain concentration of amplifier is reached. The paradoxical response concentration range begins where the highest magnitude of immune response is observed, and continues through the zone of administration of higher amplifier concentrations, said higher concentrations being associated with progressively lesser magnitudes of immune response.

What is claimed is the following:

1. A method of determining a human or animal test subject's immune response, comprising:
    (1) preparing a peripheral blood lymphocyte population from a blood sample taken from said test subject, thereby providing a first preparation;
    (2) exposing a plurality of portions of said first preparation to a means for activating suppressor cells and to different predetermined concentrations of amplifier, wherein one of said portions is exposed to no amplifier, thereby providing a control level, said portions providing a second preparation;
    (3) culturing said second preparation, thereby producing a first culture;
    (4) exposing said first culture to a means for preventing cell division, and thereafter removing any residual amount of said means from said culture, thereby producing a nonproliferating culture;
    (5) combining a further portion of a pheripheral blood lymphocyte population with said nonproliferating culture, thereby providing a responder preparation;
    (6) exposing said responder preparation to a means for inducing a cell proliferation immune response, thereby producing a third preparation;

(7) culturing said third preparation, thereby producing a second culture; and (8) determining an immune response index in said second culture.

2. The method of claim 1 wherein said subject is a human subject.

3. The method of claim 2 wherein said means of step 6 is PHA, pokeweed, concanavalin A or tetanus toxoid.

4. The method of claim 2 wherein said amplifier is Amplifier Beta.

5. The method of claim 2 wherein said amplifier is Amplifier Zeta-2.

6. The method of claim 2 wherein said amplifier is Tyr-Gly-Gly.

7. The method of claim 2 wherein said immune response index of step 8 is measurement of thymidine uptake.

8. The method of claim 7 wherein said thymidine is radioactively tagged.

9. The method of claim 2 wherein said immune response index of step 8 is measurement of interleukin-2 production.

10. The method of claim 2 wherein said immune response index of step 8 is measurement of gamma-interferon production.

11. The method of claim 2 wherein the method used for measurement of said immune response is an ELISA assay.

12. A method of determining an immune system response of a human test subject comprising:

(1) preparing a peripheral blood lymphocyte population from a blood sample taken from said subject, thereby providing a first preparation;

(2) exposing a plurality of portions of said first preparation to Concavalin A and to different predetermined concentrations of amplifier, wherein one of said portions is exposed to no amplifier, thereby providing a control level, said portions providing a second preparation;

(3) culturing said second preparation, thereby producing a first culture;

(4) exposing said first culture to mitomycin, and thereafter removing any residual amount of said mitomycin from said culture, thereby producing a nonproliferating culture;

(5) combining a further peripheral blood lymphocyte population with said nonproliferating culture, thereby providing a responder preparation;

(6) exposing said responder preparation to a mitogen or antigen, thereby producing a third preparation;

(7) culturing said third preparation, thereby producing a second culture; and (8) determining thymidine uptake in said second culture, whereby a plurality of suppressor assay results is made available.

13. The method of claim 12 wherein said portion exposed to no amplifier provides the control level for the assay from which % suppression assay results are calculated.

14. A method of determining amplifier dosage for a test subject with an autoimmune condition, comprising determining said subject's maximum % suppression assay result according to the method of claim 13, wherein:

if said maximum % suppression assay result exceeds a predetermined amount which is associate with an upper acceptable immune response level, said amplifier dosage is decreased, and if said maximum % suppression assay result is less than a predetermined amount which is associated with a lower acceptable immune response level, said amplifier dosage is increased.

15. A method of determining whether to treat with amplifier a test subject with an autoimmune condition, comprising determining said subject's maximum % suppression assay result according to the method of claim 13, wherein:

if said maximum % suppression assay result exceeds a predetermined amount which is associated with a patient's having sufficient suppressor immune reserve to warrant treatment of the patient with an amplifier for alleviation of an autoimmune disease, said subject is treated with amplifier, and if said maximum % suppression assay result is less than a predetermined amount which is associated with a patient's not having sufficient suppressor immune reserve to warrant treatment of the patient with an amplifier for alleviation of an autoimmune disease, said subject is not treated with amplifier.

16. The method of claim 15 wherein the autoimmune condition is rheumatoid arthritis.

17. The method of claim 15 wherein the autoimmune condition is lupus erythematosus.

18. The method of claim 15 wherein the autoimmune condition is diabetes mellitus, type 1.

19. The method of claim 15 wherein the autoimmune condition is multiple sclerosis.

20. A method of treating a patient with hypernormal cell-mediated immune system resonse, comprising:

determining said patient's suppressor immune reserve and base suppressor response; and if said suppressor immune reserve is not abnormally low relative to that of a normal patient, but said base suppressor response is abnormally low relative to that of a normal patient, administering to said patient a dosage of amplifier in the paradoxical response concentration range.

* * * * *